（12）United States Patent
McLaughlin et al.

(10) Patent No.: US 7,820,152 B2
(45) Date of Patent: *Oct. 26, 2010

(54) SHAVE GEL COMPOSITION CONTAINING GLYCERYL ACRYLATE/ACRYLIC ACID COPOLYMER

(75) Inventors: Ronald Patrick McLaughlin, Medford, MA (US); Ali Alwattari, Braintree, MA (US)

(73) Assignee: The Gillette Company, Boston, MA (US)

( * ) Notice: Subject to any disclaimer, the term of this patent is extended or adjusted under 35 U.S.C. 154(b) by 815 days.

This patent is subject to a terminal disclaimer.

(21) Appl. No.: 11/129,693

(22) Filed: May 13, 2005

(65) Prior Publication Data

US 2006/0257349 A1    Nov. 16, 2006

(51) Int. Cl.
*A61K 8/19*    (2006.01)
(52) U.S. Cl. ............................................ 424/73
(58) Field of Classification Search .............. None
See application file for complete search history.

(56) References Cited

U.S. PATENT DOCUMENTS

| | | | | |
|---|---|---|---|---|
| 4,863,725 | A | * 9/1989 | Deckner et al. | 514/772.4 |
| 5,326,556 | A | 7/1994 | Barnet et al. | 424/73 |
| 5,500,211 | A | 3/1996 | George et al. | 424/73 |
| 5,560,859 | A | 10/1996 | Hartmann et al. | 424/73 |
| 5,587,156 | A | 12/1996 | Wdowik | 424/73 |
| 5,858,343 | A | 1/1999 | Szymczak | 424/73 |
| 5,985,294 | A | 11/1999 | Peffly | 424/401 |
| 2002/0122772 | A1 | 9/2002 | Lukenbach et al. | 424/44 |
| 2003/0053980 | A1 | 3/2003 | Dodd et al. | 424/73 |
| 2004/0166086 | A1 | * 8/2004 | Manivannan et al. | 424/73 |
| 2005/0175575 | A1 | 8/2005 | Xu et al. | 424/73 |

FOREIGN PATENT DOCUMENTS

| EP | 0829259 | | 3/1998 |
|---|---|---|---|
| FR | 2694189 | A1 * | 2/1994 |

OTHER PUBLICATIONS

Guardian Laboratories, Lubrajel® Oil data sheet (Mar. 14, 2005).
Lubrajel® Water Soluble Emollients, Moisturizers and Thickeners, ISP (undated).
Office Action rejections/objections from co-pending application Case No. T-732, U.S. Appl. No. 10/777,009, 18 pages, filed Aug. 1, 2005.
Examiner's Answer to Appeal Brief from co-pending application Case No. T-732, U.S. Appl. No. 10/777,009, 9 pages, filed May 3, 2007.
Board's Decision co-pending application from co-pending application Case No. T-732, U.S. Appl. No. 10/777,009, 10 pages, filed Nov. 14, 2007.
Amendment dated Jul. 6, 2010, which is a reply to Office Action mailed on Feb. 3, 2010 for Application No. 11/129,694, filed May 13, 2005.

* cited by examiner

*Primary Examiner*—Robert A Wax
*Assistant Examiner*—Bethany Barham
(74) *Attorney, Agent, or Firm*—Ronald T. Sia; Kevin C. Johnson; Steven W. Miller

(57) ABSTRACT

Disclosed is a shaving composition in the form of a post-foaming gel that contains a glyceryl acrylate/acrylic acid copolymer. In particular the shaving composition comprises, in percent by weight, about 60% to about 93%, preferably about 70% to about 85%, water, about 2% to about 25%, preferably about 5% to about 20%, water dispersible (or soluble) surface active agent, about 1% to about 6%, preferably about 2% to about 5%, volatile post-foaming agent, and about 0.0005% to about 1%, preferably about 0.001% to about 0.1%, glyceryl acrylate/acrylic acid copolymer.

20 Claims, No Drawings

SHAVE GEL COMPOSITION CONTAINING GLYCERYL ACRYLATE/ACRYLIC ACID COPOLYMER

BACKGROUND OF THE INVENTION

The present invention relates to a shaving composition in the form of a post-foaming gel that contains a glyceryl acrylate/acrylic acid copolymer.

Currently, a widely used form of shaving preparation is the type referred to as a post-foaming shave gel. These post-foaming shave gels are now well-known and have been described, for example, in U.S. Pat. No. 2,995,521 (Bluard), U.S. Pat. No. 3,541,581 (Monson), U.S. Pat. No. 4,405,489 (Sisbarro), U.S. Pat. No. 4,528,111 (Su), U.S. Pat. No. 4,651,503 (Anderson), U.S. Pat. No. 5,248,495 (Patterson), U.S. Pat. No. 5,308,643 (Osipow), U.S. Pat. No. 5,326,556 (Barnet), U.S. Pat. No. 5,500,211 (George), U.S. Pat. No. 5,560,859 (Hartmann) and U.S. Pat. No. 5,858,343 (Szymczak). Such compositions generally take the form of an oil-in-water emulsion in which the post-foaming agent, generally a volatile (i.e., low boiling point) aliphatic hydrocarbon, is solubilized in the oil phase, and the water phase comprises a water-dispersible soap or interrupted soap component. The product is generally packaged in an aerosol container with a barrier, such as a piston or collapsible bag, to separate the post-foaming gel from the propellant required for expulsion of the product. The product is dispensed as a clear, translucent or opaque gel that is substantially free from foaming until it is spread over the skin, at which time it produces a foam lather generated by the volatilization of the volatile hydrocarbon foaming agent.

While currently known shave gel compositions provide excellent shaving performance, it would be highly desirable to improve the lubricity of such compositions. It would also be highly desirable to improve the gel strength of such compositions. Further, it would be highly desirable to provide a shave gel composition with improved moisturization of the skin and beard.

SUMMARY OF THE INVENTION

The present invention embraces a shaving composition in the form of a post-foaming gel that contains a glyceryl acrylate/acrylic acid copolymer. In particular the shaving composition comprises, in percent by weight, about 60% to about 93%, preferably about 70% to about 85%, water, about 2% to about 25%, preferably about 5% to about 20%, water dispersible (or soluble) surface active agent, about 1% to about 6%, preferably about 2% to about 5%, volatile post-foaming agent, and about 0.0005% to about 1%, preferably about 0.001% to about 0.1%, glyceryl acrylate/acrylic acid copolymer.

DETAILED DESCRIPTION OF THE INVENTION

The term "fatty", as used herein, means a hydrocarbon chain having 12-22 carbon atoms ($C_{12-22}$), preferably 14-18 carbon atoms ($C_{14-18}$). The chain may be straight or branched and may be saturated or unsaturated (typically one or two double bonds in the chain). The term "water dispersible", as used herein, means that a substance is either substantially dispersible or soluble in water.

The shaving composition of the present invention comprises, in percent by weight, about 60% to about 93%, preferably about 70% to about 85%, water, about 2% to about 25%, preferably about 5% to about 20%, water dispersible surface active agent, about 1% to about 6%, preferably about 2% to about 5%, volatile post-foaming agent, and about 0.0005% to about 1%, preferably about 0.001% to about 0.1%, more preferably about 0.002% to about 0.05%, glyceryl acrylate/acrylic acid copolymer.

The water dispersible surface active agent is preferably one that is capable of forming a lather and may comprise a soap, an interrupted soap, a detergent, an anionic surfactant, a non-ionic surfactant or a mixture of one or more of these. The soaps include, for example, the sodium, potassium and lower alkanolamine (preferably triethanolamine) salts of $C_{12-22}$, preferably $C_{14-18}$, fatty acids. Typical fatty acids include lauric, myristic, palmitic and stearic acid and mixtures thereof. The preferred fatty acids are palmitic and stearic. The interrupted soaps include, for example, the sodium, potassium and lower alkanolamine (preferably triethanolamine) salts of N-fatty acyl sarcosines, wherein the fatty acyl moiety has 12 to 22, preferably 14 to 18, carbon atoms. Typical sarcosines include stearoyl sarcosine, myristoyl sarcosine, palmitoyl sarcosine, oleoyl sarcosine, lauroyl sarcosine, cocoyl sarcosine and mixtures thereof. The soaps and the interrupted soaps may be utilized in preneutralized form (i.e., as the sodium, potassium or alkanolamine salt) or in the free acid form followed by subsequent neutralization with sodium hydroxide, potassium hydroxide and/or lower alkanolamine (preferably triethanolamine). In any event, the final composition must contain sufficient base to neutralize or partially neutralize the soap component and adjust the pH to the desired level (typically between 5 and 10, more typically between 6 and 9). It is most preferred that the composition of the present invention includes a soap (e.g., triethanolamine palmitate/stearate) or an interrupted soap (e.g., triethanolamine stearoyl/myristoyl sarcosinate), or a mixture thereof.

The water dispersible surface active agent may also optionally include a non-ionic, amphoteric and/or anionic surfactant. Suitable non-ionic surfactants will typically have an HLB of 9 or more and include the polyoxyethylene ethers of fatty alcohols, acids and amides, particularly those having 10 to 20, preferably 12 to 18, carbon atoms in the fatty moiety and about 2 to 60, preferably 4 to 30, ethylene oxide units. These include, for example, Oleth-20, Steareth-21, Ceteth-20, Laureth-4 and Laureth-23. Other non-ionic surfactants include the polyoxyethylene ethers of alkyl substituted phenols, such as Nonoxynol-4 and Nonoxynol-20, fatty alkanolamides such as Lauramide DEA and Cocamide MEA, polyethoxylated sorbitan esters of fatty acids, such as Polysorbate-20, lauryl polyglucoside, sucrose laurate, and polyglycerol 8-oleate. Suitable amphoteric surfactants include, for example, the betaines and sultaines such as cocoamidopropyl betaine, coco dimethyl carboxymethyl betaine, coco sultaine and the like. Suitable anionic surfactants include, for example, the sodium, potassium, ammonium and substituted ammonium salts (such as the mono-, di- and triethanolamine salts) of $C_8$-$C_{22}$, preferably $C_{12}$-$C_{18}$, alkyl sulfates (e.g., sodium lauryl sulfate, ammonium lauryl sulfate), alkyl sulfonates (e.g., ammonium lauryl sulfonate), alkylbenzene sulfonates (e.g. ammonium xylene sulfonate), acyl isethionates (e.g. sodium cocoyl isethionate), acyl lactylates (e.g. sodium cocoyl lactylate) and alkyl ether sulfates (e.g., ammonium laureth sulfate). The surface active agent may typically include up to about 10%, preferably 1 to 8%, of non-ionic, amphoteric and/or anionic surfactants.

The post-foaming agent may be any volatile hydrocarbon or halohydrocarbon with a sufficiently low boiling point that it will volatilize and foam the gel upon application to the skin, but not so low that it causes the gel to foam prematurely. The typical boiling point of such an agent generally falls within the range of −20° to 40° C. Preferred post-foaming agents are selected from saturated aliphatic hydrocarbons having 4 to 6 carbon atoms, such as n-pentane, isopentane, neopentane, n-butane, isobutane, and mixtures thereof. Most preferred is a mixture of isopentane and isobutane in a weight ratio (IP:IB) of about 1:1 to about 9:1, preferably about 2:1 to about 7:1, most preferably about 3:1. The post-foaming agent will normally be selected so as to provide a vapor pressure at 20° C. of about 3 to about 20 psig, preferably about 5 to about 15 psig. The post-foaming agent will be present in an amount to provide the shaving composition with a sufficiently rapid turnover—that is, transition from gel to foam when contacted with the skin—typically, in about 2 to about 30 seconds, preferably in about 5 to about 15 seconds.

The glyceryl acrylate/acrylic acid copolymer is highly hydrophilic, has a molecular weight greater than 1 million daltons and generally includes a polyacrylic acid backbone partially esterified (typically about 50% esterified) with glycerin. It is believed that the glyceryl acrylate/acrylic acid copolymer forms a clathrate that holds water, which, upon release, supplies lubrication and moisturization to the skin. It has been found that shave gel compositions that include the glyceryl acrylate/acrylic acid copolymer have improved gel structure and reduced coefficient of friction (i.e., increased lubricity). A preferred source of glyceryl acrylate/acrylic acid copolymer is available from ISP Technologies, Inc. (United Guardian Inc.) under the tradename Lubrajel®, particular the form known as Lubrajel® oil which contains about 1.0%-1.3% glyceryl acrylate/acrylic acid copolymer in aqueous glycerin (~40% glycerin). Lubrajel® oil also includes about 0.6% PVM/MA copolymer (also known as methoxyethylene/maleic anhydride copolymer), which may further contribute to the lubricity of this source. Preferably, the shave gel composition will include about 0.25% to about 4% Lubrajel® oil in order to provide a preferred level of about 0.002% to about 0.05% of the glyceryl acrylate/acrylic acid copolymer. This amount of Lubrajel® oil will also provide about 0.001% to about 0.03% of PVM/MA copolymer.

Although not necessary to forming a useful shave gel composition, other cosmetic ingredients may be advantageously added to improve the application aesthetics and/or achieve other shave benefits. For example, the composition may include one or more of the following components: beard wetting agents, skin conditioning agents (e.g., vitamins A, C and E, aloe, allantoin, panthenol, alpha-hydroxy acids, phospholipids, triglycerides, botanical oils, amino acids), foam boosters, emollients, humectants (e.g., glycerin, sorbitol, propylene glycol), fragrances, colorants, antioxidants, preservatives, etc. It is particularly preferred to include glycerin in the shave gel composition of the present invention, preferably in an amount of about 0.1% to about 3%, more preferably about 0.3% to about 1%, by weight. Glycerin improves the emolliency and lubricity of the composition.

It may also be desirable to include an ester of a fatty acid, typically in an amount of about 0.5% to about 5%, preferably about 1% to about 4%, by weight. Useful fatty esters include glyceryl fatty esters such as, for example, glyceryl oleate and glyceryl dioleate, and fatty alcohol esters such as, for example, isostearyl linoleate, isocetyl oleate, and isostearyl isostearate. These materials provide emolliency, lubrication and gel structure.

The shave gel composition may include a water-soluble gelling aid or thickening agent to improve its consistency and stability, as well as to adjust its viscosity. These may include, for example, hydroxyalkyl cellulose polymers such as hydroxyethyl cellulose and hydroxypropyl cellulose (sold under the trademarks "Natrosol" and "Klucel" respectively), PEG-150 distearate, carboxymethyl cellulose, and cellulose methyl ether (sold under the trademark "Methocel"). Other suitable materials include the polysaccharide gums such as, for example, xanthan gum, carrageenan gum, guar gum, locust bean gum, and hydroxypropyl guar gum. The gelling aid or thickening agent is typically included in an amount of about 0.01% to 5%, preferably about 0.1% to 2%, by weight of the composition.

For increased lubricity, the shaving composition may include a lubricious water soluble polymer, typically in an amount of about 0.005% to about 2%, preferably about 0.01% to about 1%, by weight. Such polymers will typically have a molecular weight between about 300,000 and 15,000,000 daltons. Suitable polymers include, for example, polyvinylpyrrolidone, polyethylene oxide and polyacrylamide. A preferred shave gel composition will include a lubricious water soluble polymer, particularly a polyethylene oxide, and more particularly a polyethylene oxide with a molecular weight of about 1 to about 5 million daltons. Particularly suitable polyethylene oxides include, for example, PEG-23M (MW≅1 million), PEG-45M (MW≅2 million) and PEG-90M (MW≅4 million).

For increased lubricity, the shaving composition may include polytetrafluoroethylene ("PTFE") particles, preferably micronized PTFE particles. Preferably these particles will have an average particle size of about 1 μm to about 100 μm, more preferably about 2 μm to about 50 μm, and most preferably about 5 μm to about 15μm. The PTFE particles reduce the measured coefficient of friction between the razor cartridge and the user's skin, as compared to the coefficient of friction that would be obtained when using the same shaving preparation without the polymer particles. Suitable polytetrafluoroethylene particles include those commercially available from Micro Powders, Inc. under the tradename MICROSLIP.

Preferably the polymer particles are dispersed uniformly throughout the shave gel composition. The particles may be used in any amount that improves lubricity and glide without undesirably compromising the other attributes of the shaving preparation. Generally, the composition will include from about 0.01% to about 5%, preferably about 0.1% to about 2%, of the PTFE particles.

Preferably, the shaving composition of the present invention will include at least one lubricious polymer selected from the aforementioned lubricious water soluble polymers (e.g., polyethylene oxide) and PTFE particles. More preferably, the shaving composition will include both a lubricious water soluble polymer, such as polyethylene oxide, and PTFE particles.

The shaving compositions of the present invention may be packaged in any suitable dispenser normally used for dispensing shaving gels. These include collapsible tubes, pump or squeeze containers, and aerosol-type dispensers with a barrier to separate the shaving composition from the propellant required for expulsion. The latter type of dispensers include: (1) mechanically pressurized bag-in-sleeve systems in which a thin-walled inner bag containing the product is surrounded by an outer elastic sleeve that is expanded during the product filling process and provides dispensing power to expel the product (e.g., the ATMOS System available commercially from the Exxel Container Co.); (2) manually activated air pump spray devices in which a pump system is integrated into the container to allow the user to pressurize the container with air in order to expel the product (e.g., the "AIRSPRAY" system available from Airspray International); (3) piston barrier systems in which the product is separated from the driving means by a tight-fitting piston which seals to the side of the container and may be driven by a spring under tension, by a vacuum on the product side of the piston, by finger pressure, by gas pressure to the piston, or by a variety of other means known to the packaging industry; and (4) bag-in-can (SEPRO) systems in which the product is contained in a flexible bag within a can, with a suitable propellant injected into the space between the can and the flexible bag. It is preferred to protect the composition from oxidation and heavy metal contamination. This can be achieved, for example, by purging the composition and container with nitrogen to remove oxygen and by utilizing inert containers (e.g., plastic bottles or bags, aluminum cans or polymer coated or lined cans).

The invention may be further described by the following examples in which all parts and percentages are by weight (unless otherwise indicated).

EXAMPLES 1-5—POST-FOAMING SHAVE GEL

| Ingredient | Weight Percent | | | | |
|---|---|---|---|---|---|
| | Ex. 1 | Ex. 2 | Ex. 3 | Ex. 4 | Ex. 5 |
| Water | 78.24 | 75.02 | 75.94 | 75.55 | 75.64 |
| Triethanolamine | 5.88 | 5.88 | 5.88 | 5.88 | 5.88 |
| Palmitic acid | 7.53 | 7.53 | 7.53 | 7.53 | 7.53 |
| Stearic acid | 2.53 | 2.53 | 2.53 | 2.53 | 2.53 |
| Glyceryl Oleate | 1.94 | 1.94 | 1.94 | 1.94 | 1.94 |
| PEG-23M | 0.05 | 0.05 | 0.05 | 0.05 | 0.05 |
| PEG-90M | | 0.06 | 0.06 | 0.06 | 0.06 |
| Hydroxyethylcellulose | 0.49 | 0.49 | 0.49 | 0.49 | 0.49 |
| Lubrajel oil* | 0.49 | 0.97 | 0.49 | 0.97 | 0.49 |
| Sorbitol | | 0.97 | 0.97 | 0.97 | 0.97 |
| Glycerin | | 0.49 | | | 0.49 |
| PTFE powder | | 0.15 | 0.15 | 0.15 | 0.15 |
| Fragrance | | 0.87 | 0.78 | 0.78 | 0.78 |
| Colorant | | 0.10 | 0.29 | 0.19 | 0.10 |
| Other (e.g. Vit. E, Aloe, etc.) | | 0.10 | 0.05 | 0.06 | 0.05 |
| Isopentane/isobutane (3:1) | 2.85 | 2.85 | 2.85 | 2.85 | 2.85 |

*Lubrajel oil contains 1.0%-1.3% Glyceryl Acrylate/Acrylic Acid Copolymer (MW ≅ 1 million)

The above-described compositions are made in the following manner: The water soluble polymers (polyethylene oxide, hydroxyethylcellulose) are added to water and mixed until the polymers are completely dissolved (about 30 min.). The aqueous mixture is then heated and the glyceryl oleate, sorbitol and fatty acids are added at about 60° C. and well mixed while the heating continues. At 80-85° C. the triethanolamine is added and mixed for about 20 minutes to form the aqueous soap phase. After cooling the aqueous soap phase to room temperature, the remaining components (i.e., Lubrajel, glycerin, fragrance, colorant, botanicals) are added to the aqueous soap phase and mixed well to form the gel concentrate. (Water may be added if required to bring the batch weight to 100%, thereby compensating for any water loss due to evaporation.) The concentrate is then combined with the volatile post-foaming agent under pressure within the filling line and filled into bottom-gassed aerosol cans with shearing through the valve under nitrogen pressure.

The above-described shave gel compositions of the present invention provide superior lubrication and gel strength, compared to similar compositions that do not include a glyceryl acrylate/acrylic acid copolymer.

While particular embodiments of the invention have been shown and described for illustrative purposes, it will be apparent to those skilled in the art that various changes and modifications may be made without departing from the spirit and scope of the invention, which is defined by the claims which follow.

What is claimed is:

1. A shaving composition in the form of a post-foaming gel comprising, in percent by weight, about 60% to about 93% water, about 2% to about 25% water dispersible surface active agent, about 1% to about 6% volatile post-foaming agent, about 0.0005% to about 1% glyceryl acrylate/acrylic acid copolymer, and a gelling aid or thickening agent that is different than the glyceryl acrylate/acrylic acid copolymer; and
   a package,
   wherein a single shaving composition is contained within the package.

2. The shaving composition of claim 1 wherein the composition comprises, in percent by weight, about 70% to about 85% water, about 5% to about 20% water dispersible surface active agent, about 2% to about 5% volatile post-foaming agent, and about 0.001% to about 0.1% glyceryl acrylate/acrylic acid copolymer 3. The shaving composition of claim 2 comprising about 0.002% to about 0.05% glyceryl acrylate/acrylic acid copolymer.

4. The shaving composition of claim 1 wherein the water dispersible surface active agent comprises a soap or an interrupted soap.

5. The shaving composition of claim 2 wherein the water dispersible surface active agent comprises a soap or an interrupted soap.

6. The shaving composition of claim 3 wherein the water dispersible surface active agent comprises a soap or an interrupted soap.

7. The shaving composition of claim 1 additionally comprising glycerin or sorbitol or a mixture thereof.

8. The shaving composition of claim 5 additionally comprising glycerin or sorbitol or a mixture thereof.

9. The shaving composition of claim 1 additionally comprising one or more lubricious polymers selected from the group consisting of polyethylene oxide and polytetrafluoroethylene.

10. The shaving composition of claim 5 additionally comprising one or more lubricious polymers selected from the group consisting of polyethylene oxide and polytetrafluoroethylene.

11. The shaving composition of claim 9 additionally comprising glycerin or sorbitol or a mixture thereof.

12. The shaving composition of claim 10 additionally comprising glycerin or sorbitol or a mixture thereof.

13. The shaving composition of claim 1 wherein the glyceryl acrylate/acrylic acid copolymer has a molecular weight greater than 1 million and comprises a polyacrylic acid backbone approximately 50% esterfied with glycerin.

14. The shaving composition of claim 5 wherein the glyceryl acrylate/acrylic acid copolymer has a molecular weight greater than 1 million and comprises a polyacrylic acid backbone approximately 50% esterfied with glycerin.

15. The shaving composition of claim 1 additionally comprising PVM/MA copolymer.

16. The shaving composition of claim 3 additionally comprising about 0.001% to about 0.03% of PVM/MA copolymer.

17. The shaving composition of claim 6 additionally comprising about 0.001% to about 0.03% of PVM/MA copolymer.

18. A shaving composition in the form of a post-foaming gel comprising: about 60% to about 93%, in percent by weight, water, a water dispersible surface active agent; a volatile post-foaming agent; a gelling aid or thickening agent; and a lubrication system comprising the combination of a glyceryl acrylate/acrylic acid copolymer, a lubricous water soluble polymer, and polytetrafluoroethylene particles, and a package, wherein a single shaving composition is contained within the package.

19. The shaving composition of claim 18 wherein the polytetrafluoroethylene particles have an average particle size of from about 2 μm to about 50 μm.

20. The shaving composition of claim 18 wherein the polytetrafluoroethylene particles have an average particle size of from about 5 μm to about 15 μm.

* * * * *